United States Patent [19]

Schneiderman

[11] Patent Number: 4,498,475
[45] Date of Patent: Feb. 12, 1985

[54] ELECTROSURGICAL UNIT

[75] Inventor: Max Schneiderman, Clifton, N.J.

[73] Assignee: Ipco Corporation, White Plains, N.Y.

[21] Appl. No.: 412,230

[22] Filed: Aug. 27, 1982

[51] Int. Cl.$^3$ ............................................. A61B 17/39
[52] U.S. Cl. .......................... 128/303.14; 128/303.17; 323/911
[58] Field of Search ...................... 128/303.13, 303.14, 128/303.17, 303.18, 421-423; 323/911

[56] References Cited

U.S. PATENT DOCUMENTS

| | | | |
|---|---|---|---|
| 3,707,149 | 12/1972 | Hao et al. | 128/303.14 |
| 3,875,945 | 4/1975 | Friedman | 128/303.14 |
| 4,014,347 | 3/1977 | Helleck et al. | 128/422 |
| 4,051,855 | 10/1977 | Schneiderman | 128/303.14 |
| 4,092,986 | 6/1978 | Schneiderman | 128/303.14 |
| 4,281,373 | 7/1981 | Mabille | 128/303.14 X |

FOREIGN PATENT DOCUMENTS 2737172 2/1979 Fed. Rep. of Germany ........................ 128/303.13

Primary Examiner—Lee S. Cohen
Attorney, Agent, or Firm—Goodman & Teitelbaum

[57] ABSTRACT

An electrosurgical unit for producing a modulated oscillating signal for coagulation procedures and an unmodulated oscillating signal for cutting procedures. The unit includes a four arm bridge rectifier interconnected directly to the line voltage. A first pair of opposing diagonal terminals on the rectifier is connected directly to the line voltage. A cutting signal is obtained from the other pair of diagonal terminals, and a coagulation signal is obtained across one arm of the bridge rectifier. An oscillator tank coil provides the necessary RF isolation output. A switch selectively interconnects either the coagulation signal output from the bridge rectifier, or the cutting signal output from the bridge rectifier, to the oscillator. The output is taken across the tank circuit from the RF oscillator and applied to a patient through a handpiece. Through the use of high voltage transistors in the circuit, high efficiency is obtained by eliminating the input transformer of the prior art.

19 Claims, 5 Drawing Figures

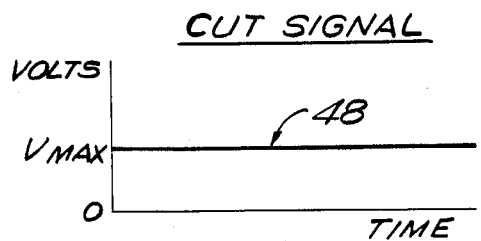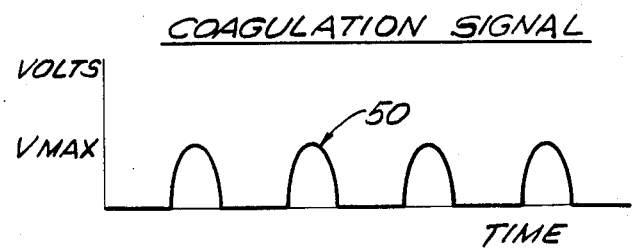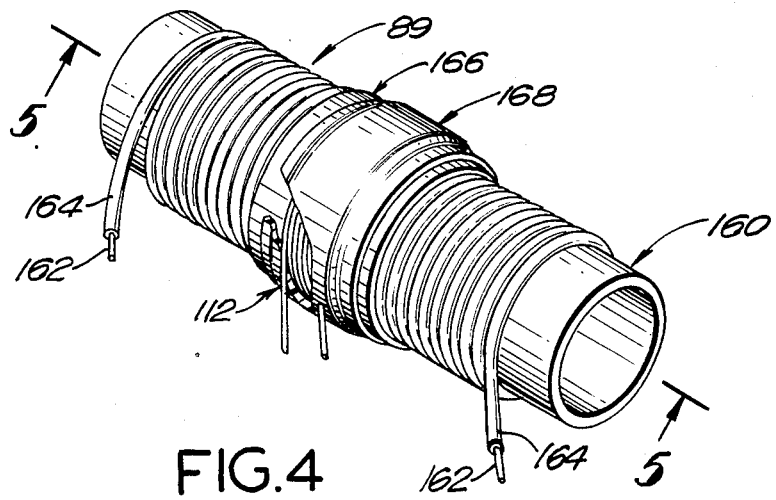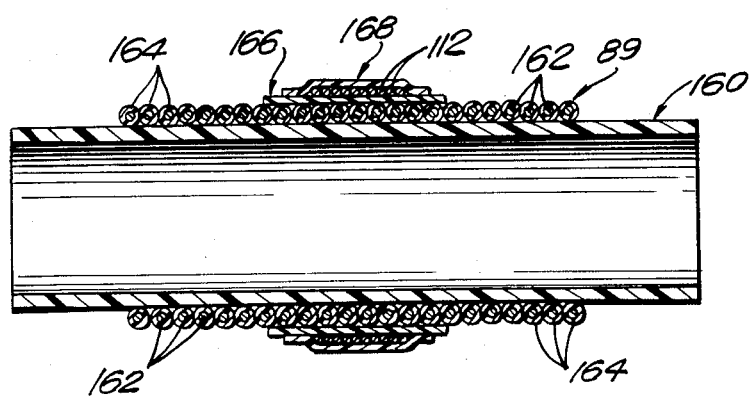

ELECTROSURGICAL UNIT

BACKGROUND OF THE INVENTION

This invention relates to an electrosurge, and more particularly to an electrosurgical device which provides an unmodulated RF signal for tissue cutting procedures, and a modulated RF signal for coagulation procedures.

Electrosurge units are well known in the prior art for utilization in the field of surgery. Such units typically include an oscillator which provides an output at an RF frequency. Modulation means are included which can be selectively operated to modulate the oscillation output. With the RF energy modulated, it has been found that the output is effective in coagulating blood vessels. Without the modulation, the continuous RF signal itself is effective in cutting tissue and can be utilized as an electrosurgical device during an operating procedure. Typically, a handpiece such as a probe or forceps is utilized to apply the modulated and/or unmodulated output to the patient during an operation.

The electrosurgical units of the prior art have been described in numerous patents. One effective electrosurgical unit has been described in U.S. Pat. No. 4,051,855, assigned to the assignee of the present invention which describes an electrosurgical unit utilizing vacuum tube devices and producing an ungrounded output to avoid hazards such as burns which can occur if the patient would touch a grounded output unit.

Another electrosurge unit has been described in U.S. Pat. No. 4,092,986, also assigned to the assignee of the present invention, and which also utilizes a vacuum tube oscillator and includes a level adjustment device to provide a constant output electrosurge voltage. Still a further electrosurgical unit is described in U.S. Pat. No. 4,301,801 also assigned to the assignee of the present invention which further adds a fail-safe system to the circuit so as to disconnect the power supply to the electrosurge generator in the event of a failure at the output.

While all of these, as well as many other electrosurges, have been found effective, all these devices include a power transformer between the power supply and the electrosurge unit, where many of these devices use vacuum tubes. This power transformer provides isolation at the input of the unit as well as providing the necessary conversion of voltage needed to operate the electrosurge unit itself. With the availability of transistors, it is now possible to avoid the use of a vacuum tube oscillator. However, utilization of a power transformer has still caused transformer losses to the system which substantially reduced its efficiency. Furthermore, it has increased the size, cost and weight of the unit, and made it both bulky and awkward in design.

It is noted, that in order to market the electrosurgical devices, these devices must have the ability to withstand the conventional UL/C.S.A. 2500 volt dielectric strength test, which is well known in the art.

SUMMARY OF THE INVENTION

It is therefore an object of the present invention to provide an electrosurge which avoids the aforementioned problems of the prior art devices.

Another object of the present invention is to provide an electrosurgical unit operating directly off the line without the use of a power transformer.

A further object of the present invention is to provide an electrosurgical unit as set forth above, which has the ability to withstand the UL/C.S.A. 2500 volt dielectric strength test.

A further object of the present invention is to provide an electrosurgical unit as set forth above, which uses a reed relay and a special RF coil to achieve the above results.

Yet another object of the present invention is to provide an electrosurgical unit which eliminates the use of a power transformer at the input and thereby eliminates transformer losses to thereby improve the efficiency of the unit.

Still a further object of the present invention is to provide an electrosurgical unit which utilizes high voltage transistors which can operate directly from the line without the need of power transformers.

A further object of the present invention is to provide an electrosurgical unit which utilizes a bridge rectifier directly across the line without the use of a power transformer and obtains the modulating signal as well as the unmodulating signal directly from the bridge rectifier.

Another object of the present invention is to provide an electrosurgical unit which utilizes a bridge rectifier directly across the line, wherein the internal voltage is supplied directly from the rectifier.

A further object of the present invention is to provide an electrosurgical unit which utilizes transistors for the RF generator, and avoids the necessity of utilizing vacuum tube circuitry.

A further object of the present invention is to provide an electrosurgical unit which includes an intensity control unit and an ON/OFF switch, and wherein ON/OFF switching is accomplished at minimum setting of the intensity control thereby assuring that switching transients never occur during maximum power output.

Still another object of the present invention is to provide an electrosurgical unit which includes pilot lights indicating utilization of either the cutting output or the coagulating output, and whereby the pilot lights utilize capacitive voltage drops to avoid power dissipation in the voltage drop element.

Yet a further object of the present invention is to provide an electrosurgical unit having a reed relay which defines an internal ON/OFF switch within the unit.

Another object of the present invention is to provide an electrosurgical unit having a transistorized oscillator with an RF tank coil, wherein the tank coil provides isolation to the patient utilizing the unit.

Another object of the present invention is to provide an electrosurgical unit having an output RF tank coil formed with an improved construction.

Another object of the present invention is to provide an electrosurgical unit having an RF oscillator whose components are selected such that in the event of inadvertent application of an excess load, the oscillator will stop and go into its standby mode thereby avoiding damage.

A further object of the present invention is to provide an electrosurgical unit which is higher in efficiency, reduced in cost as well as size, and improved in operation as compared to prior art devices.

Briefly, in accordance with the present invention, there is provided an electrosurgical unit for producing a modulated oscillating signal for coagulation procedures, and an unmodulated oscillating signal for cutting procedures. The electrosurgical unit includes a four-arm bridge rectifier which is interconnected by two pairs of diagonally opposing terminals. A first pair of opposing terminals is directly connected to the line voltage of the power source. A cutting output signal is obtained across the other pair of opposing terminals. A coagulation signal output is obtained across one arm of the bridge. An oscillator is provided which produces an RF output signal of a desired frequency. A switching device can selectively couple either the coagulation signal output or the cutting signal output to the oscillation device to thereby produce the modulated or unmodulated oscillating signal for the cutting and coagulating procedures.

In an embodiment of the present invention, a pair of indicator lights are provided. A selector is operatively connected to the switching device for selecting one of the indicator lights and placing it across the first pair of opposing terminals of the bridge. A reactive device, such as a capacitor, is connected in series with the selector to provide a substantially quadrature relationship between the voltage and current thereby providing the necessary voltage drop without providing any power dissipation.

In another embodiment of the present invention, an intensity control is included, and the intensity control includes an internal ON/OFF switch which is controlled by means of a reed relay which in turn is energized through a transformer connected to the line voltage.

The entire unit is formed of high voltage transistor devices and, accordingly, the rectifier can be connected directly to the power line without the need of a power transformer at the input, thereby eliminating losses normally introduced by the transformer. Power limitations are then confined to the transistor and the output RF coil characteristics.

The electrosurgical unit of the present invention has the ability to withstand the UL/C.S.A. 2500 volt dielectric strength test.

BRIEF DESCRIPTION OF THE DRAWINGS

With the above and additional objects and advantages in view, as will hereinafter appear, this invention comprises the devices, combinations, and arrangements of parts hereinafter described by way of example and illustrated in the accompanying drawings of a preferred embodiment in which:

FIG. 2 shows a constant DC level signal provided at the cut output contact;

FIG. 3 shows the waveshape of the modulating signal provided at the coagulation output contact;

FIG. 4 is a fragmented perspective view of the output coil assembly in accordance with the present invention; and FIG. 5 is a cross sectional view taken along line 5—5 of FIG. 4.

In the various figures of the drawing, like reference characters designate like parts.

DESCRIPTION OF THE PREFERRED EMBODIMENT

Figure 1:
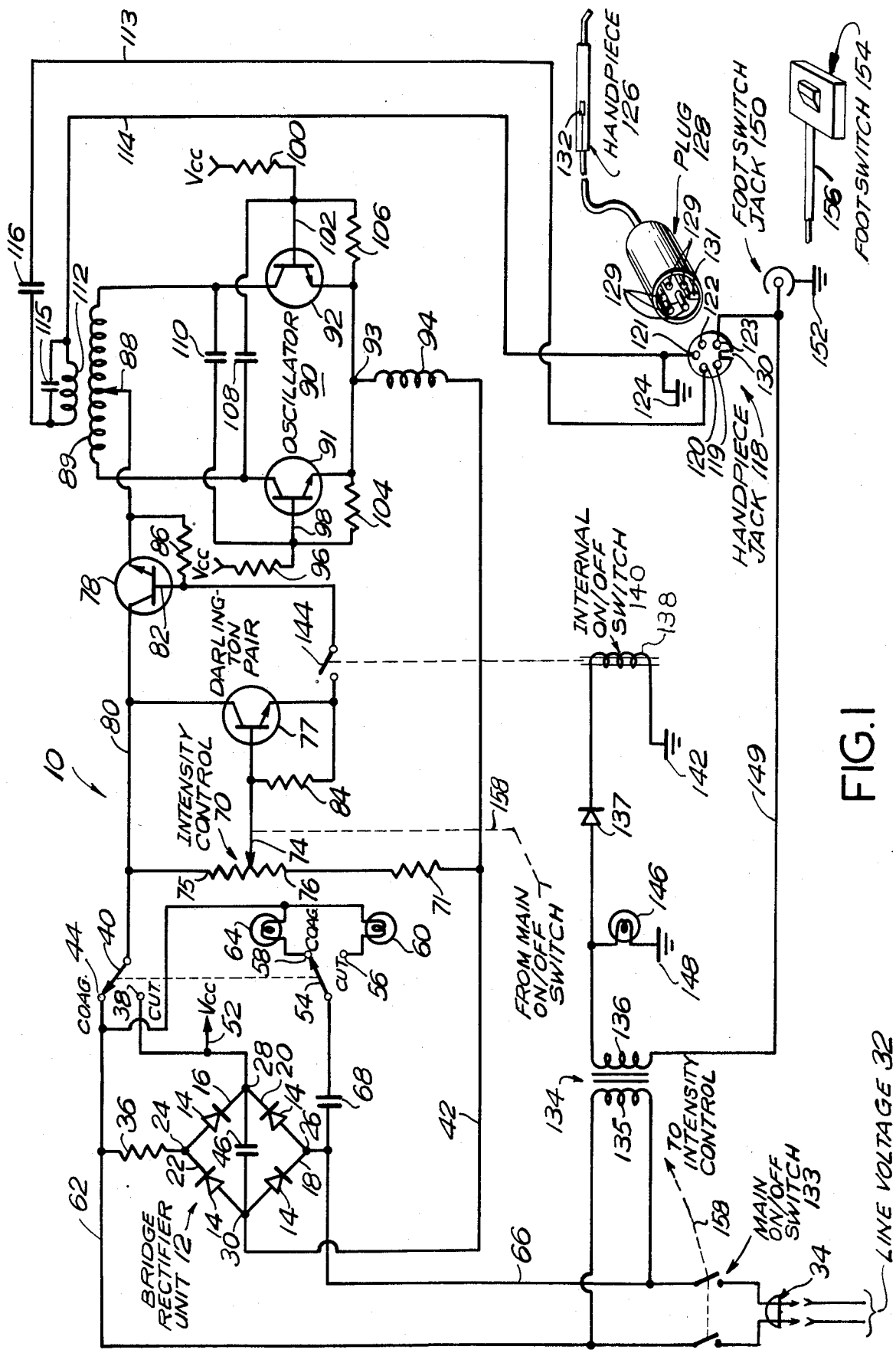
FIG. 1 is a schematic electrical drawing of the present invention.

Referring now to FIG. 1, there is shown a schematic electrical drawing of the electrosurge 10 of the present invention, which includes a bridge rectifier unit 12 formed of diodes 14 contained in respective opposing arms 16, 18 and opposing arms 20, 22. The arms 16, 22 are interconnected at the terminal 24, and an opposing terminal 26 interconnects arms 18 and 20. The opposite pair of opposing terminals 28, 30 form the final interconnections of the bridge with terminal 28 interconnecting arms 16 and 20 and terminal 30 interconnecting arms 18 and 22. The bridge rectifier unit 12 is connected directly across the line voltage 32 by means of a conventional plug 34 which can be directly interconnected into a wall socket. A suitable current limiting resistor 36 is included between one of the terminals of the plug 34 and the terminal 24. Accordingly, the line voltage 32 is placed directly across a first pair of opposing terminals 24, 26.

A first output, referred to as the cut output, is provided between an opposing pair of terminals 28 and 30. Terminal 28 is connected to a contact point 38 of the switch 40 and designates the cut output contact. The opposing terminal 30 forms the floating internal common ground 42 of the system. Accordingly, the cutting output voltage is provided between the contact point 38 and the line 42.

A second output, referred to as the coagulation output, is taken essentially across one arm of the bridge, specifically shown as arm 22. More particularly, the modulation output is taken from terminal 24, which is connected to a contact point 44 of the switch 40 and designates the coagulation output contact. The modulation output voltage accordingly appears between the contact point 44 and the line 42. This voltage, however, is essentially the voltage across the single bridge arm 22.

There is also provided a capacitor 46, which is interconnected between terminals 28 and 30 of the bridge rectifier unit 12. The capacitor 46 provides a parallel capacitor across the DC output taken between the contact point 38 and the line 42. This capacitor 46 serves as a filter.

Assuming that the input line voltage is a sinusoidal signal, as is typically provided, this signal will be placed across a first pair of opposing diagonal terminals 24, 26 of the bridge rectifier unit 12. As is well known, the signal taken across the opposing pair of terminals 28, 30 would be a full wave rectified signal. However, because of the inclusion of the capacitor 46, the signal which is provided at the cut output contact 38, is shown in FIG. 2 at curve 48, essentially representing a constant DC level signal.

On the other hand, since the coagulation signal taken on contact point 44 is the signal across a single arm 22, that signal will be as shown in FIG. 3 in the waveshape 50, which represents a modulating signal. Thus, by utilizing the four arm bridge rectifier, and appropriately taking the outputs at specified points across the rectifier, it is possible to utilize the rectifier for providing both the modulating and unmodulating signal for subsequent use in creating the necessary cutting and coagulation signal. Accordingly, no separate modulating multivibrator or pulse circuit need be utilized since both the DC level as well as the pulse signal is taken directly from the bridge.

It should also be appreciated, that the same DC level signal 48 which is utilized as the cutting signal, represents an unmodulated DC level which can also be applied as the Vcc signal at point 52 for the internal forward biasing of the transistors in the oscillator circuit, as set forth below. It should be appreciated, that the transistors which are utilized are of the high voltage type typically utilized in solid state TV sweep circuitry, and the like.

Accordingly, because of the fact that the transistor circuits can now utilize the high voltage level, and because of the use of the bridge rectifier, it is possible to place the rectifier directly across the line voltage. This eliminates the need of a power transformer heretofore utilized between the power supply circuit and the power source. By elimination of the power transformer, the inherent losses, which the transformer normally introduces into the circuit, are thereby avoided. As a result, there is an almost loss-less source of power provided for the RF oscillator. The only power limitations produced in the circuit are confined to the transistors and the RF coil characteristics, as will hereinafter be explained.

The switch 40 is utilized to select either the cut contact point 38 or the coagulating contact point 44 to provide the output as desired. Ganged to the switch 40, is provided a selection switch 54 which can select either a cut contact terminal 56 or a coagulating contact terminal 58. An indicator lamp 60 is connected between the contact terminal 56 and the line 62 provided directly from the one terminal of the plug 34. Similarly, an indicator bulb 64 is connected to the contact terminal 58, and is also interconnected to the line 62 from the one terminal of the plug 34. The switch 54 is coupled to the other terminal of the plug 34 by the line 66. Accordingly, with the plug 34 connected to the line voltage 32, closure of the switch 54 onto either of the contact terminals 56 or 58 respectively energizes one of the indicator bulbs 60 or 64. Thus, when the coagulation output is desired, placing the switch 40 onto the contact point 44 automatically causes switch 54 to simultaneously close onto contact terminal 58, thereby energizing the indicator 64 indicating a coagulation procedure is now in effect. Similarly, closure of the switch 44 onto the contact point 38 to select the cut output, will also cause the switch 54 to close onto its contact terminal 56, thereby energizing the indicator lamp 60 indicating a cut procedure is in effect.

In order to provide the necessary voltage for the indicator bulbs, it is necessary to provide a suitable voltage drop. Typically, a resistor is utilized in the prior art for such voltage drop. However, in place of the usual voltage dropping resistor, there is provided a capacitor 68 in the present invention. Such capacitor 68 produces a 90 degree phase angle between the voltage and current, whereby no power is dissipated in the voltage dropping element thereby avoiding any internal heat sources while obtaining the benefit of using indicator lamps.

Connected across the main selection switch 40 and line 42, there is provided an intensity control 70 system utilizing a fixed voltage dropping resistor 71 in series with a variable resistor 72 having a contact arm 74. Typically, a potentiometer or other similar device can be utilized for the variable resistor 72. Placement of the contact arm 74 at its uppermost position 75 provides for maximum voltage while placement at its lowermost position 76 provides for minimum voltage.

The output from the contact arm 74 is fed to the base of a first NPN transistor 77 connected as part of a Darlington pair in conjunction with another NPN transistor 78. The collector-emitter circuit of the first transistor 77 is connected between the main line 80 and the base 82 of the second transistor 78. Accordingly, the transistor 77 serves as the control for the second transistor 78, as is well known in Darlington pair operation. A suitable base emitter resistor 84 is connected across the transistor 77, and a corresponding base emitter resistor 86 is connected across the transistor 78 for proper functioning of the transistors 77, 78.

By controlling the positioning of the contact arm 74 along the resistor 72, a suitable drive voltage is provided onto the base of the transistor 77, which in turn controls the amount of current flowing through the transistor 78. The collector-emitter circuit of the transistor 78 is connected directly along the main line 80 providing the current toward the center tap 88 of an RF tank output coil 89 associated with the oscillator 90, as will hereinafter be described.

The oscillator 90 is a well known type of oscillator having two transistors 91, 92 connected in a balanced feedback fashion with both of their emitters interconnected to a common terminal 93, which in turn is connected to the floating internal ground line 42 through a choke 94. The internal Vcc from the bridge taken from point 52 is provided through a suitable resistor 96 to the base 98 of transistor 91, and similarly through a resistor 100 to the base 102 of the transistor 92, to provide a constant forward biasing for the respective transistors 91, 92. A base emitter resistor 104 is coupled across the transistor 91, and a corresponding base emitter resistor 106 is coupled across the transistor 92 for proper functioning of the transistors 91, 92.

The collector of transistor 91 is interconnected to the base of transistor 92 through a capacitor 108. Similarly, the collector of transistor 92 is interconnected to the base of transistor 91 through a capacitor 110. The collectors respectively interconnect to opposing ends of the coil 89. In this manner, suitable oscillations are produced by means of the tank circuit including the coil 89 and the capacitors 108, 110. The values of the capacitors are chosen such that in the event of an inadvertent application of an excess load, such as a short circuit, the oscillator will simply stop and go into a standby mode. This serves as an extra security measure to avoid damage to the case of a short circuit of the output of the electrosurgical unit.

The operation of the RF generator 90 has been found to be almost 90–95% efficient, with the only losses being introduced by means of the particular transistors and the RF coil characteristics.

The output from the RF tank is taken across a secondary coil 112 which is connected at opposite ends to lines 113, 114, the coil 112 being provided with a parallel capacitor 115. A series capacitor 116, typically serving as an isolation capacitor, is placed in the line 113 of the output circuit. The lines 113, 114 are coupled to a handpiece jack 118 having socket terminals 119, 120, 121, 122 and 123.

The RF signal itself is fed by lines 113, 114 to the socket terminals 121, 120, respectively, with the socket terminal 121 being grounded at 124. A suitable handpiece 126 is provided which has a conventional plug 128 having suitable pins 129 for insertion into the socket terminals of the jack 118. The jack 118 can also be provided with a female opening 130 to receive a male prong 131 of the plug 128 to insure proper alignment and placement of the pins 129 with their associated socket terminals 119–123. Preferably, a suitable ON/OFF switch 132 is placed directly on the handpiece 126.

The turning on and off of the electrosurgical unit 10 can be achieved by means of a main ON/OFF switch 133 connected directly between the plug 34 and the unit. Additionally, a transformer 134 is connected across the main line with the primary coil 135 connected directly across the lines 62, 66. The secondary coil 136 is connected through a diode 137 to a coil 138 of a reed relay switch 140, whose other terminal is grounded at 142. When the coil 138 of the reed relay switch 140 is energized, the switch contacts 144 of the reed relay switch 140 will be closed, as set forth below.

The contacts 144 are interconnected in series between the transistors 77 and 78. Thus, energization of the reed relay switch 140 will in turn close the switch contacts 144 so that the transistor 78 will permit current to pass from line 80 to the tank circuit 89 to thereby provide an output voltage. The switch contacts 144 effectively provide an internal ON/OFF switch which must be closed before operation will begin.

An ON/OFF indicator lamp 146 can be provided across the secondary coil 136, having its other end connected to ground at 148, to thereby indicate that the complete system has been turned on, as set forth below. It should be understood, that all of the indicator lamps 146, 60 and 64 could be placed on a front panel in view of the operator.

One end of the secondary coil 136 of the transformer 134 is interconnected by the line 149 to the center terminal of a foot switch jack 150 whose other terminal is grounded at 152. The secondary coil 136 is also interconnected by the line 149 to the socket terminal 123 of the handpiece jack 118. Accordingly, until either one of the jack 150 or the jack 118 has its contacts closed, the secondary coil 136 will not be operative. Such interconnection can be provided by means of a foot switch 154 being placed in the on position, the foot switch 154 having a plug 156 which can be interconnected into the jack 150, or alternately, by means of the handpiece 126 being placed in the on position when its plug 128 is interconnected into the jack 118.

It is noted, that no lines are connected to the socket terminals 119, 122 of the handpiece jack 118, whereby these two socket terminals can be used as desired for a future purpose not included in the present invention.

The operation of the unit will therefore first be controlled by means of the main ON/OFF switch 133 which must be closed. The turning on of the switch 133 energizes the bridge rectifier unit 12, whereby one of the indicator lamps 60, 64 is energized responsive to the selection of the switches 40, 54, and additionally the transformer 134 is placed in a standby condition. Therefore, even after that switch 133 is closed, no output signal will be provided until the operator either depresses the foot switch 154 or closes the switch 132 provided on the handpiece 126, and only after such foot or handpiece switch closure will there be an output voltage provided. According, before providing the output voltage, selection is made on the switches 40, 54 to determine whether a coagulation or cutting output is to be produced, the selection being indicated by one of the lamps 60 or 64. Therefore, until the operator actually desires the output voltage, there is avoided any possibility of an output voltage provided by accident. Thus, the operator himself must operate the foot switch or handpiece in order to provide the output voltage, this operation being performed after first determining whether a coagulation or cutting voltage is needed. This avoids the possibility of having a patient harmed by an output voltage which otherwise would continuously be provided on the device.

Upon closure of the foot or handpiece switch, the transformer 134 is activated, and thus the reed relay switch 140 is energized to close the switch contacts 144 so that the transistor 78 permits current to pass from line 80 to the tank curcuit 89, as set forth above, to thereby provide the output voltage. The closure of the foot or handpiece switch is indicated by the energization of the indicator lamp 146, also caused by the activation of the transformer 134, so that the operator is informed that the complete system has been turned on.

The main ON/OFF switch 133 is ganged with the intensity control indicator arm 74, as shown by the broken line 158. This assures that the main ON/OFF switch 133 can only be energized when the intensity control 70 is at its minimum position 76. In this way, ON/OFF switching is accomplished at the minimum setting of the intensity control 70 to assure that the switching transients never occur during maximum power output.

Utilizing the system of the present invention as shown, isolation of the patient is not provided by a power transformer at the input of the unit, as heretofore provided in the prior art. Instead, isolation occurs by means of the RF tank coils 89 and 112 at the output side of the unit. The activation system including the reed relay switch 140 and the transformer 134 is such as to withstand the standard UL/C.S.A. dielectric strength test normally required for such devices.

The particular RF tank coils 89, 112 heretofore described can preferably be formed in an improved manner, as shown in FIGS. 4 and 5. The tank coils are formed on a center sleeve 160 fabricated from insulation material, which is first wound with the primary winding coil 89 consisting of a plurality of turns. The primary coil wires are PVC insulated wire having a central wire 162 with an outer PVC insulation 164. The use of this PVC insulated wire provides insulation, and also provides the spacing desired between the turns.

Over the layer of the primary winding coil 89 is a sheet insulation material 166, such sheet material 166 being typically supplied on power transformers. On top of the layer of sheet insulation material 166, there is wound the secondary coil 112. The wire of the secondary coil 112 is typically a close-wound enameled wire. In this manner, the primary-to-secondary isolation is excellent and will easily withstand the UL/C.S.A. dielectric strength testing. The overall assembly is then encapsulated with the insulation material 168, in order to effect good heat dissipation and to maintain the structural rigidity thereof.

With the heretofore described circuit, there is achieved an extremely high efficient system which enables the design of high power electrosurges in very small packages. By way of example, the present design has been found capable of delivering 116 watts into 500 ohms with a package size of $5\frac{1}{4} \times 5\frac{3}{4} \times 2\frac{1}{2}$ inches for a total volume of 68 cubic inches. This provides approximately 1.7 watts per cubic inch.

The above compares to a prior art electrosurgical unit which delivers 68 watts in a package size of $11 \times 6\frac{3}{4} \times 5$ inches for a total volume of 371 cubic inches. This provides an output of 0.18 watts per cubic inch.

With the particular design provided in the present invention, it is practical to utilize the present electrosurgical unit not only in dentistry but also in numerous fields of hospital surgery. For example, it may be capable of utilizing the present unit in many thoracic and urinary tract operations. The very high degree of isolation available from the output tank coil is of beneficial value as well.

Numerous alterations of the structure herein disclosed will suggest themselves to those skilled in the art. However, it is to be understood that the present disclosure relates to a preferred embodiment of the invention which is for purposes of illustration only and is not to be construed as a limitation of the invention.

What is claimed is:

1. An electrosurgical unit for producing from a power source a modulated oscillating signal for coagulation procedures and an unmodulated oscillating signal for cutting procedures, comprising:

a four-arm bridge rectifier having two pairs of diagonally opposing terminals, means for directly coupling a first pair of said opposing terminals to the power source, filter means coupled across said other pair of said opposing terminals for smoothing the signal at said opposing terminals, cutting signal output means coupled across said other pair of said opposing terminals and producing a fixed level signal, coagulation signal output means coupled across one arm of said bridge rectifier, and producing a modulating signal;

oscillation means for producing an oscillating output signal at a given frequency; and switching means for selectively coupling one of said output means directly to said oscillation means to selectively provide the signals from the oscillation means to thereby produce an unmodulated and a modulated signal.

2. An electrosurgical unit as in claim 1, and further comprising local output means coupled across said filter means for obtaining a local DC signal for use in operating components within said electrosurgical unit.

3. An electrosurgical unit as in claim 1, and further comprising a pair of indicator means, selection means operatively coupled to said switching means for selectively placing one of said indicator means across said first pair of said opposing terminals, and reactive means coupled in series with said selection means for producing a substantially quadrature relationship between the voltage and the current thereacross, to provide voltage dropping without power dissipation.

4. An electrosurgical unit as in claim 3, wherein said reactive means is a capacitor.

5. An electrosurgical unit as in claim 1, and further comprising intensity control means coupled between said switching means and said oscillation means for selectively limiting the output power of said electrosurgical unit to a desired level.

6. An electrosurgical unit as in claim 5, wherein said intensity control means includes a resistor coupled across said oscillation means, a variable tap coupled to said resistor, a Darlington connected pair of transistors, a control element of one of said transistors coupled to said variable tap, and the main flow path of the other of said transistors being serially connected between said switching means and said oscillation means.

7. An electrosurgical unit as in claim 6, and further comprising activation circuit means for activating said electrosurgical unit, said activation circuit means having an initiating switch coupled between said first pair of said opposing terminals and the power source.

8. An electrosurgical unit as in claim 7, and comprising coupling means for operatively coupling said initiating switch to said intensity control means so that closure of said initiating switch can only occur at a minimum setting of said intensity control means, whereby switching transients can only occur at minimum power output.

9. An electrosurgical unit as in claim 7, wherein said activation circuit means includes a reed relay energized after closure of said initiating switch and having its contacts in series between said pair of Darlington connected transistors.

10. An electrosurgical unit as in claim 9, and comprising transformer means for coupling said reed relay to the power source for producing isolation of the activation circuit means from the power source.

11. An electrosurgical unit as in claim 10, wherein said reed relay is connected in series with said transformer means and is available for external activation of said electrosurgical unit, said oscillation means being placed in a standby condition upon closure of said initiating switch.

12. An electrosurgical unit as in claim 1, wherein said oscillation means comprises a pair of balanced feedback connected transistors, and capacitor means coupled between a base of one transistor and a collector of the other transistor, whereby upon application of an excessive load, such as a short circuit, said oscillation means will drop out.

13. An electrosurgical unit as in claim 1, wherein said bridge rectifier is isolated from an earth ground so that both said modulated and unmodulated signals operate with a floating internal ground.

14. An electrosurgical unit as in claim 1, comprising an output tank coil coupled to said oscillation means, and application means for applying the output from the electrosurgical unit, said tank coil providing isolation and transformer action between said application means and said oscillation means.

15. An electrosurgical unit as in claim 14, wherein said tank coil comprises a primary coil coupled to said oscillation means, said tank coil being wound of PVC insulated wire, a layer of insulation covering said primary coil, a secondary coil wound over said insulation layer, said secondary coil being an enameled wire, and encapsulation means covering said primary and secondary coils to effect good heat dissipation and structural rigidity thereof.

16. An electrosurgical unit for producing a modulated oscillating signal for coagulation procedures and an unmodulated oscillating signal for cutting procedures, comprising:

a four-arm bridge rectifier having two pairs of diagonally opposing terminals, means for coupling a first pair of said opposing terminals to a power source, cutting signal output means coupled across the other pair of said opposing terminals and producing a fixed level signal, coagulation signal output means coupled across one arm of said bridge rectifier and producing a modulated signal;

oscillation means for producing an output signal at a given frequency;

switching means for selecting one of said output means from said rectifier;

coupling means for interconnecting the output selected by said switching means to said oscillation means;

activation circuit means for activating said electrosurgical unit, said activation circuit means having an initiating switch coupled between said first pair of said opposing terminals and the power source, and a reed relay energized from the power source after closure of said initiating switch and having its contacts in series with said coupling means to prevent coupling of the selected output to the oscillation means until its contacts are closed.

17. An electrosurgical unit as in claim 16, and comprising transformer means for coupling said reed relay to the power source for producing isolation of the activation circuit means from the power source.

18. An electrosurgical unit as in claim 17, wherein said reed relay is connected in series with said transformer means and is available for external activation of said electrosurgical unit, said oscillation means being placed in a standby condition upon closure of said initiating switch.

19. An electrosurgical unit as in claim 17, and comprising a manual operating unit means for operative control by an operator of the unit, a control switch means on said manual operating unit means for energizing said reed relay, whereby said selected output signal is produced upon closure of said initiating switch and said switching means, but is only coupled to said oscillation means under control of the operator through said control switch means.

* * * * *